(12) United States Patent
Sobotka

(10) Patent No.: US 9,274,063 B2
(45) Date of Patent: Mar. 1, 2016

(54) BUILDING INSPECTION DEVICE

(75) Inventor: Jozef Sobotka, Mississauga (CA)

(73) Assignee: FTD Highrise Inspection Inc., Mississauga, Ontario (CA)

( * ) Notice: Subject to any disclaimer, the term of this patent is extended or adjusted under 35 U.S.C. 154(b) by 472 days.

(21) Appl. No.: 13/884,157

(22) PCT Filed: Oct. 18, 2011

(86) PCT No.: PCT/CA2011/001163
§ 371 (c)(1),
(2), (4) Date: May 8, 2013

(87) PCT Pub. No.: WO2012/061922
PCT Pub. Date: May 18, 2012

(65) Prior Publication Data
US 2013/0235185 A1    Sep. 12, 2013

Related U.S. Application Data

(60) Provisional application No. 61/413,155, filed on Nov. 12, 2010.

(51) Int. Cl.
*E04G 3/00* (2006.01)
*G01N 21/95* (2006.01)
(Continued)

(52) U.S. Cl.
CPC *G01N 21/95* (2013.01); *E04G 3/34* (2013.01); *G01M 5/0025* (2013.01); *G01M 5/0091* (2013.01); *G01N 21/88* (2013.01); *G01N 29/225* (2013.01); *G01N 33/00* (2013.01)

(58) Field of Classification Search
CPC .......... E04G 3/34; G01N 21/95; G01N 21/88; G01N 33/00; G01M 5/0025; G01M 5/0091
USPC .................................... 104/89–95
See application file for complete search history.

(56) References Cited

U.S. PATENT DOCUMENTS 4,550,376 A * 10/1985 Maciejczak ........... G01M 99/00
348/82
4,625,938 A * 12/1986 Brown ................... F16M 11/18
248/550

(Continued)

FOREIGN PATENT DOCUMENTS

JP          2767643 B2      6/1998
WO       WO9933272         7/1999
(Continued)

OTHER PUBLICATIONS

Hicks, "Building Envelope Condition Assessment and Commissioning," Proceedings of the RCE 23rd International Convention, pp. 113-120.

(Continued)

*Primary Examiner* — Jason C Smith
(74) *Attorney, Agent, or Firm* — Kagan Binder, PLLC

(57) ABSTRACT

The invention is a building inspection device for inspecting a side of a building comprising a body having a underside, a line attachment means connected to the body for movably connecting the body to a guide line, an alignment means for aligning the body so that the underside of the body faces the side of the building, a system controller for controlling the inspection device, and a sensing device disposed in the body having a sensor located on the underside of the body for inspecting a portion of the side of the building, wherein the sensing device is controlled by the system controller. The line attachment means may be connected to a vertical weight-bearing guide line, and the alignment means may comprise a second vertical guide line also connected to the line attachment means.

20 Claims, 8 Drawing Sheets

(51) Int. Cl.
*G01M 5/00* (2006.01)
*G01N 21/88* (2006.01)
*E04G 3/34* (2006.01)
*G01N 29/22* (2006.01)
*G01N 33/00* (2006.01)

(56) References Cited

U.S. PATENT DOCUMENTS

| | | | | |
|---|---|---|---|---|
| 4,789,947 A | | 12/1988 | Maciejczak | |
| 4,958,306 A | * | 9/1990 | Powell | G01C 7/04 702/40 |
| 4,993,913 A | * | 2/1991 | Ohtsuki | B25J 5/00 180/901 |
| 5,103,739 A | * | 4/1992 | Sawada | H02G 1/02 104/112 |
| 5,585,707 A | * | 12/1996 | Thompson | B25J 5/00 318/568.1 |
| 5,652,617 A | * | 7/1997 | Barbour | E21B 47/0002 348/85 |
| 5,809,099 A | * | 9/1998 | Kim | G21C 17/013 250/559.33 |
| 6,028,625 A | * | 2/2000 | Cannon | G01M 11/081 348/135 |
| 6,040,853 A | * | 3/2000 | Delagnes | G01C 7/04 348/128 |
| 6,512,536 B1 | * | 1/2003 | Ross | G01B 11/105 348/61 |
| 6,636,581 B2 | * | 10/2003 | Sorenson | G01N 23/04 378/58 |
| 6,711,284 B1 | * | 3/2004 | Koide | G06T 7/0004 382/141 |
| 6,793,026 B1 | * | 9/2004 | De Fazio | A63H 11/04 180/8.3 |
| 7,634,966 B2 | * | 12/2009 | Pouliot | H02G 1/02 104/112 |
| 8,660,698 B2 | * | 2/2014 | Phillips | H02G 1/02 700/259 |
| 8,666,553 B2 | * | 3/2014 | Phillips | B60K 16/00 700/259 |
| 2001/0015149 A1 | * | 8/2001 | Montambault | H02G 1/02 104/112 |
| 2003/0128030 A1 | * | 7/2003 | Hintze | G01N 27/902 324/217 |
| 2006/0235611 A1 | * | 10/2006 | Deaton | G01C 15/00 701/491 |
| 2006/0287835 A1 | * | 12/2006 | Sheth | G01M 5/0025 702/35 |
| 2006/0290779 A1 | * | 12/2006 | Reverte | E03F 7/10 348/84 |
| 2007/0235238 A1 | * | 10/2007 | Sadegh | B62D 49/0621 180/164 |
| 2008/0276823 A1 | * | 11/2008 | Montambault | B61B 7/06 104/173.1 |
| 2013/0235185 A1 | * | 9/2013 | Sobotka | G01M 5/0025 348/125 |

FOREIGN PATENT DOCUMENTS

| | | |
|---|---|---|
| WO | WO2005/045545 | 5/2005 |
| WO | WO2008000677 | 1/2008 |

OTHER PUBLICATIONS

Tso et al., "Robot Assisted Wall Inspection for Improved Maintenance of High-Rise Buildings," Department of Manufacturing Engineering and Engineering Management, pp. 449-455.

* cited by examiner

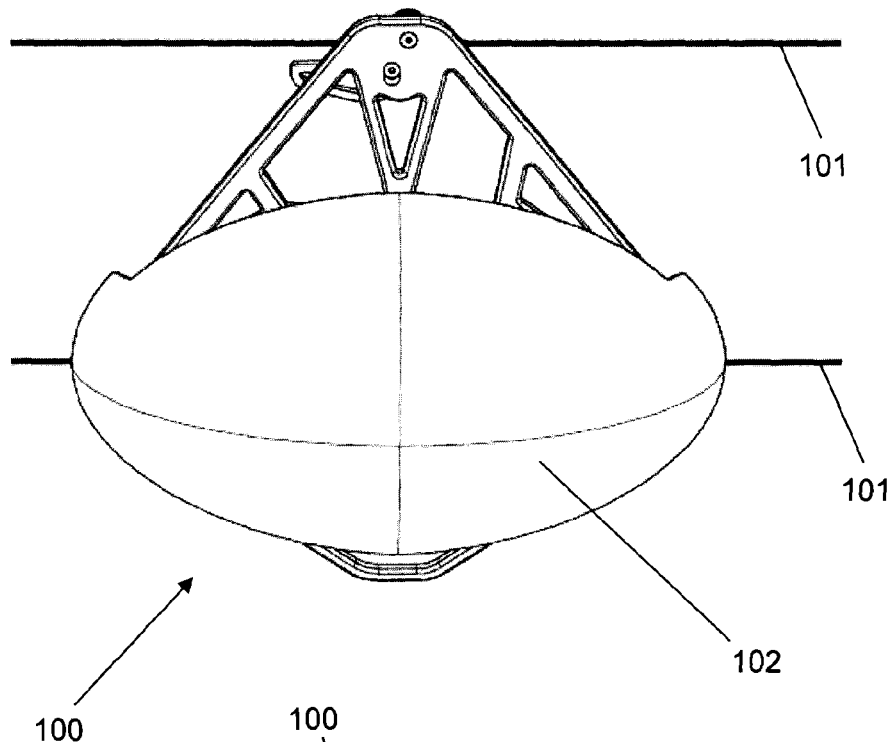
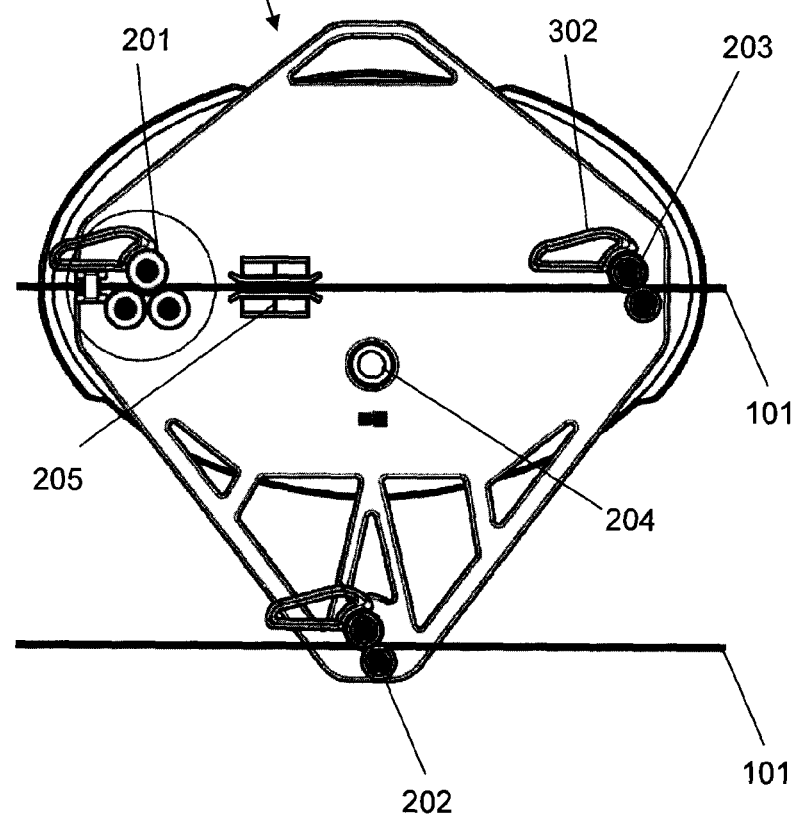

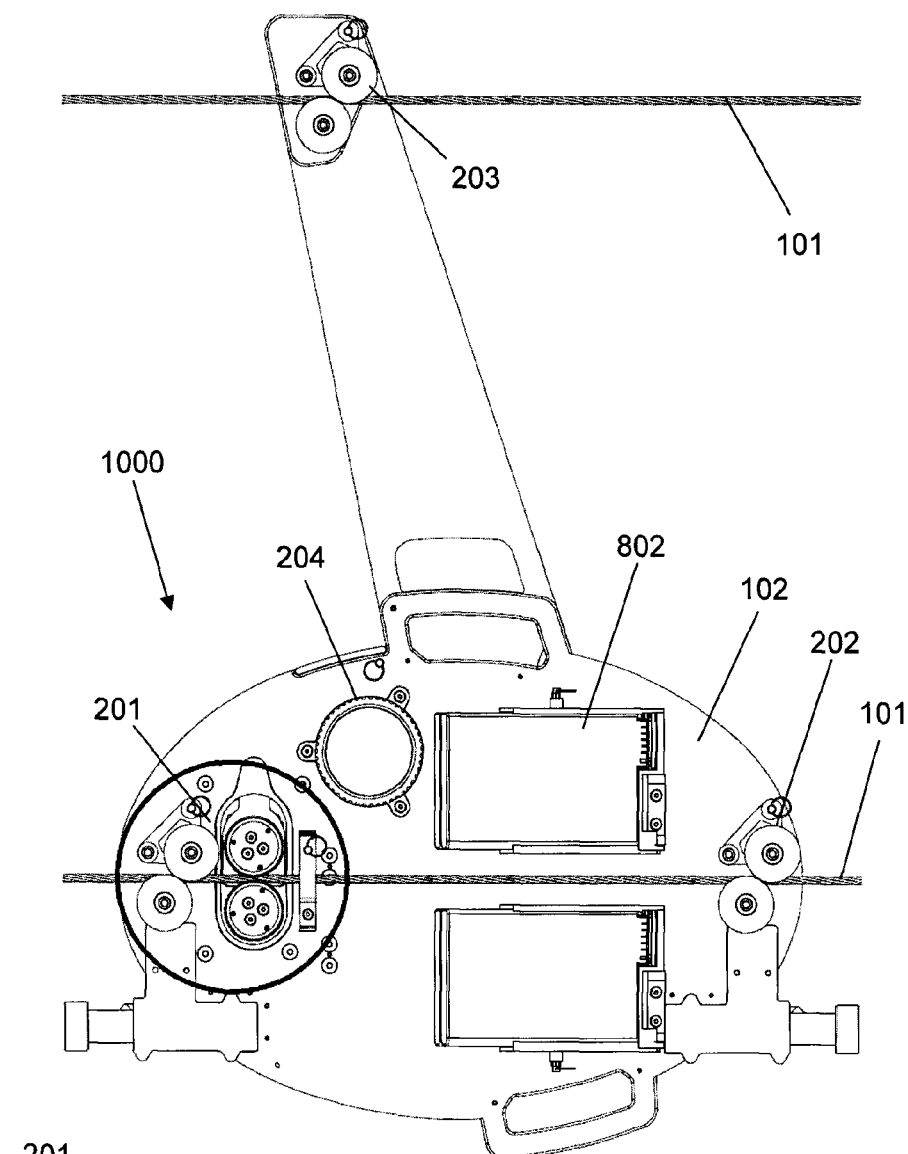
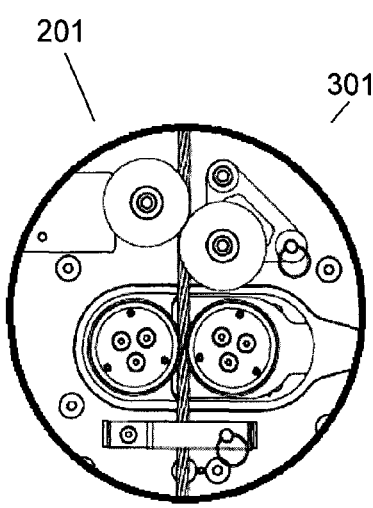
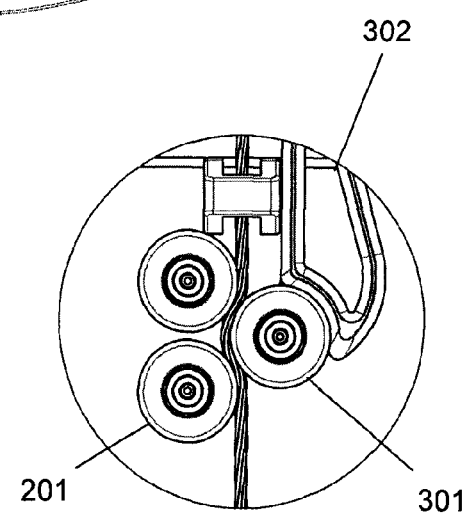
Figure 5
Figure 5a
Figure 2a

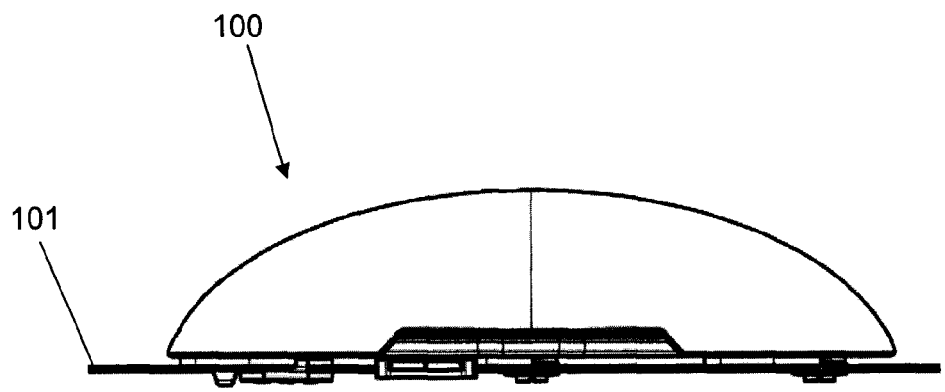
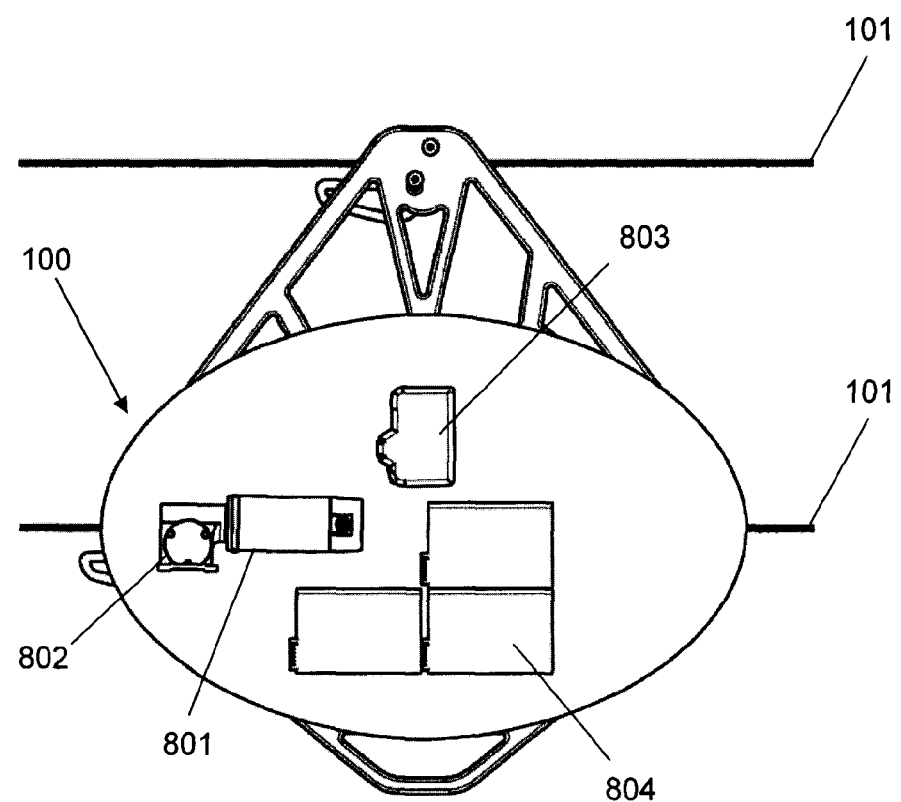

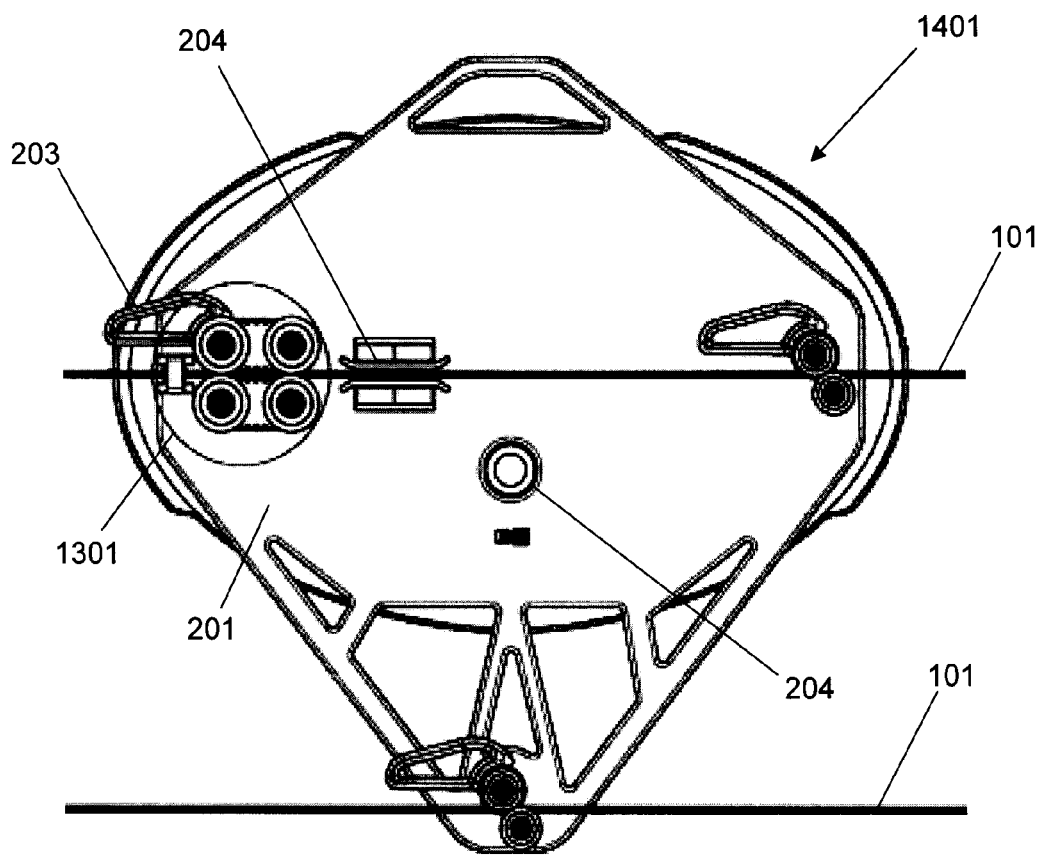
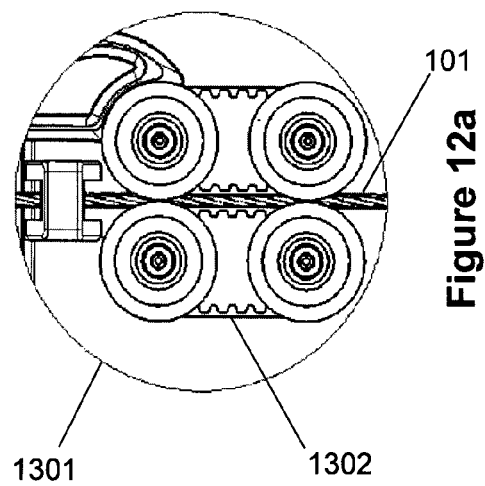
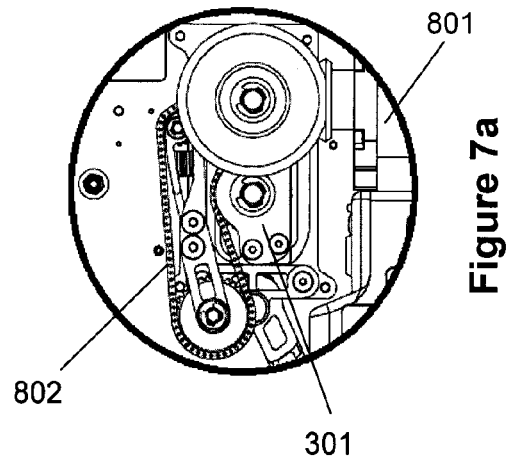

BUILDING INSPECTION DEVICE

RELATED APPLICATION

This application claims the benefit from International Application No. PCT/CA2011/001163, filed Oct. 18, 2011, which in turn claims the benefit of U.S. Provisional Patent Application Ser. No. 61/413,155, filed Nov. 12, 2010, which applications are incorporated herein by reference in their entireties.

FIELD OF THE INVENTION

The present invention relates generally to a system and method for inspecting surfaces of a structure, and more particularly, to a system and method for inspecting the exterior walls of a building.

BACKGROUND OF THE INVENTION

Exterior building inspections are an important aspect of high-rise monitoring and maintenance. Inspecting the walls of a building for damage or flaws can be expensive, time-consuming and dangerous. Inspections are commonly conducted by workmen.

SUMMARY OF THE INVENTION

The invention is directed to an inspection system comprising: at least one guide line, a rooftop rigging system to suspend the at least one guide line alongside a structure, the rigging system comprising a cantilevered section that is configured to overhang a side of the structure to position the at least one guide line, a base tensioning system configured to couple to an end of the at least one guide line spaced from the rooftop rigging system and stabilize the at least one guide line alongside a structure, a structure inspection device configured to move along the at least one guide line and document the condition of a structure exterior, the inspection device comprising a drive train to propel the inspection device along the at least one guide line, an imaging system to document the exterior condition of a structure and a control system to control and documentation of the structure exterior condition and movement of the inspection device along the at least one guide line.

The invention is further directed to an inspection device comprising: an imaging system to document the condition of a structure disposed adjacent the inspection device, a drive train to propel the inspection device along a weight bearing guide line, the drive train comprising a set of wheels, including a drive wheel, that are configured to grip the weight bearing guide line, and a drive motor coupled to the drive wheel to rotate the drive wheel and propel the inspection device along the guide line, a stabilizer configured to orientate the imaging system relative to a structure, and a control system to autonomously control documentation of the structure exterior condition and propulsion of the inspection device along the guide lines.

The invention is further directed to a method of documenting a structure comprising: coupling an inspection device to a set of guide lines suspended alongside a structure, calibrating the inspection device by setting a drive increment, the drive increment defining the distance between adjacent imaging locations, propelling the inspection device along the guide lines between discrete imaging locations, retaining the inspection device in position at each imaging location and capturing an image of the structure, and determining imaging sequence completion for a strip of the structure defined by the guide lines.

The invention is further directed to an inspection device comprising: an imaging system to document the condition of a structure, a drive train to propel the inspection device along a set of guide lines disposed adjacent a structure, and a control system configured to: receive calibration input indicative of the spacing of the inspection device from the structure and determine a drive increment, the drive increment defining the distance between adjacent imaging locations, activate the drive train to propel the inspection device along the guide lines between discrete imaging locations, retain the inspection device in position at each imaging location and capturing an image of the structure, and determine imaging sequence completion for a strip of the structure defined by the guide lines.

BRIEF DESCRIPTION OF THE DRAWINGS

FIG. 1 is a perspective top view of a building inspection device mounted to a pair of guide lines. The inspection device comprises a stabilizing outrigger that mounts to a stabilizing guide line and a body that mounts to a weight bearing guide line. The top of the inspection device body of the inspection device is covered by a cowling.

FIG. 2 is an underside elevation of the inspection device illustrated in FIG. 1. The inspection device is coupled to the guide lines by three sets of wheels disposed in a triangular configuration. Two sets of wheels, including the drive train wheels, are mounted to the body of the inspection device and are coupled to the weight bearing guide line. These wheels are disposed fore and aft along an approximate longitudinal centerline of the inspection device body. Another set of wheels (stabilizing runners) are disposed on the outrigger, laterally offset from the inspection device body, and are coupled to a stabilizing guide line.

FIG. 2a is an exploded view of the drive train wheels illustrated in FIG. 2.

FIG. 3 is a side elevation of the inspection device illustrated in FIGS. 1 and 2 coupled to a pair of guide lines.

FIG. 4 is a top elevation of the inspection device illustrated in FIGS. 1-3 with the outer cowling removed. The inspection drive motor, transmission, imaging system and batteries are illustrated mounted to the top of the inspection device body in positions that are covered by the cowling when attached.

FIG. 5 is an underside elevation of another embodiment of inspection device also coupled to a pair of guide lines. The inspection device comprises a stabilizing outrigger that mounts to a stabilizing guide line and a body that mounts to a weight bearing guide line. The device batteries are mounted to the underside of the inspection device body. Similarly to the inspection device illustrated in FIGS. 1 to 4, the device is coupled to the guide lines by three sets of wheels disposed in a triangular configuration. Two sets of wheels, including the drive train wheels, are mounted to the body of the inspection device and are coupled to the weight bearing guide line. These wheels are disposed fore and aft along an approximate longitudinal centerline of the inspection device body. Another set of wheels (stabilizing runners) are disposed on the outrigger, laterally offset from the inspection device body, and are coupled to a stabilizing guide line.

FIG. 5a is an exploded view the drive train illustrated in FIG. 5 attached to the weight bearing guide line. The drive train comprises a pair of biased drive wheels that grip the weight bearing guide line. A pair of drive train runners is disposed below the drive train wheels and defines the path of the guide line through the drive train wheels.

FIG. 7a is an exploded view of the drive train illustrated in FIG. 7. The drive motor is coupled to the primary drive wheel by a bevel gear between. A chain couples the primary drive wheel to a secondary drive wheel. The chain is arranged so that the secondary drive wheel is rotated in an opposing direction to the primary drive wheel. The secondary drive wheel is mounted in a sliding bracket that is seated in a housing in the inspection device body.

FIG. 12 is an underside elevation of an inspection device incorporating a drive train utilizing a belt track to grip the weight bearing guide line. The drive train comprises four wheels divided by the guide line path into two sets of two wheels. Each set of wheels are arranged generally parallel with the guide line path. Each wheel set is coupled by a belt.

FIG. 12a is an exploded view of the drive train illustrated in FIG. 12. The drive train comprises two drive wheels disposed on either side of the guide line path. Each drive wheel is coupled to a runner disposed on the same side of the guide line path by a belt. The weight bearing guide line is illustrated between the opposing sets of coupled wheels being gripped by the respective belts.

DETAILED DESCRIPTION

Figure 6:
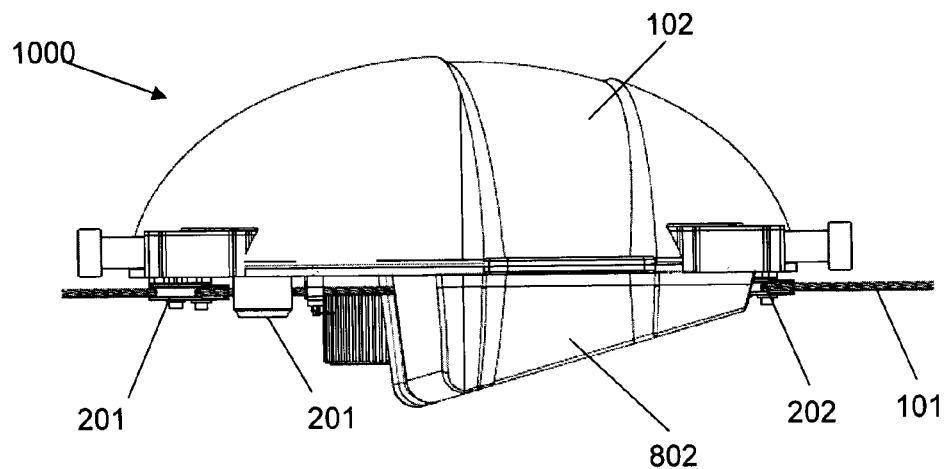
FIG. 6 is a side elevation of the inspection device illustrated in FIGS. 4 and 5 with a cowling covering the top of the inspection device body. The batteries are arranged in an angled configuration on the underside of the inspection device body on either side of the weight bearing guide line.
Figure 7:
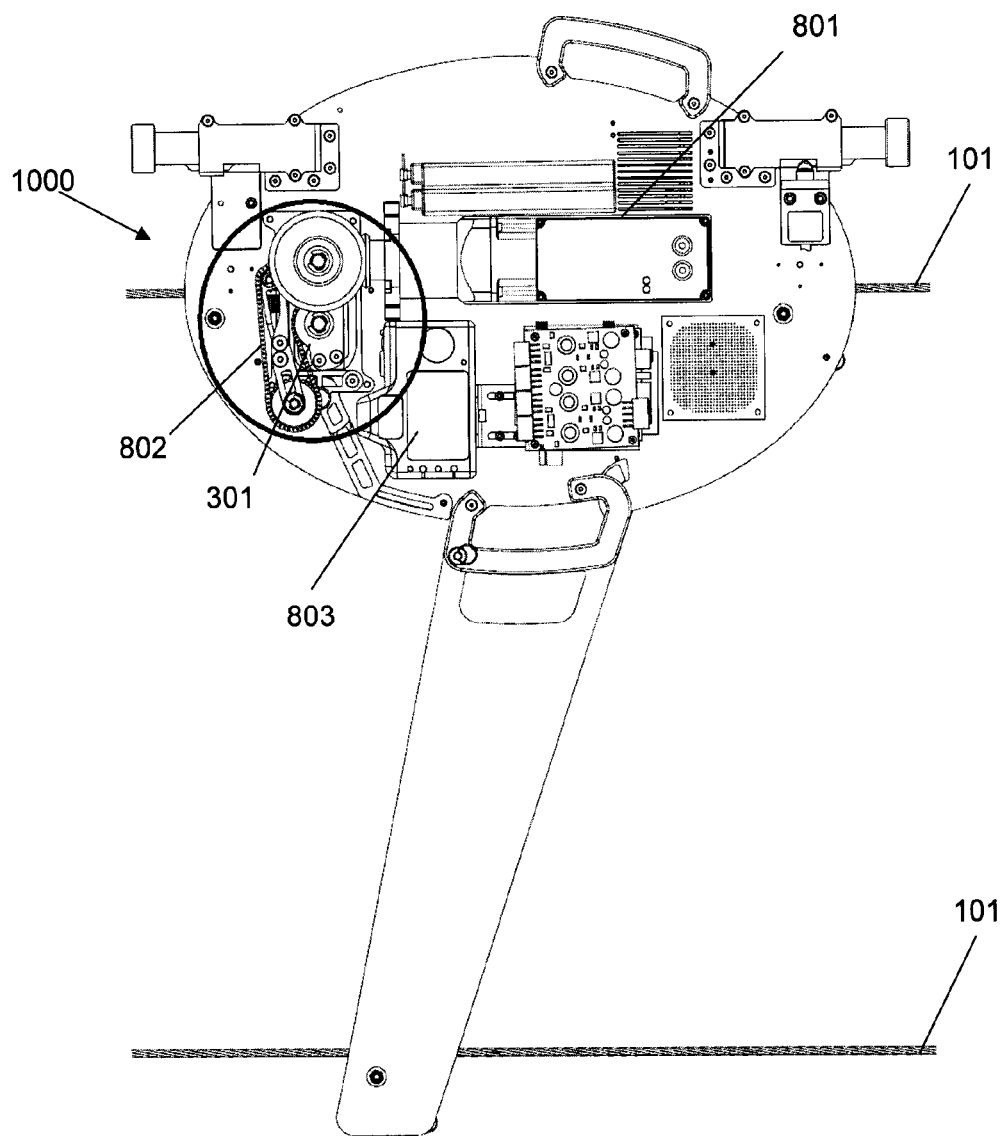
FIG. 7 is a top elevation of the inspection device illustrated in FIGS. 4 to 6 with the cowling removed. The drive motor, transmission, imaging system and control system are illustrated mounted to the top of the inspection device body in positions that are covered by the cowling when attached.
Figure 8:
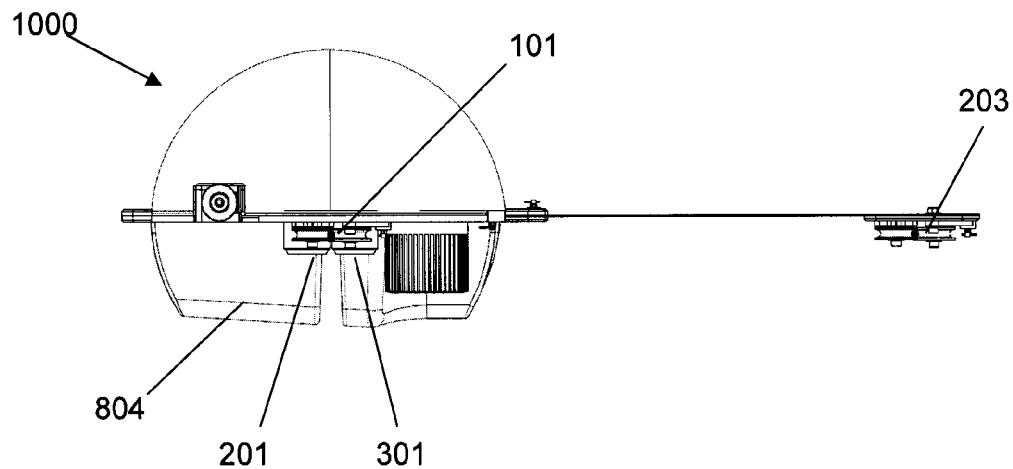
FIG. 8 is a front elevation of the inspection device illustrated in FIGS. 4 and 7 with a cowling covering the top of the inspection device body. The batteries are arranged in an angled configuration on the underside of the inspection device body on either side of the weight bearing guide line.

A building inspection device and system is illustrated in FIGS. 1 to 12. The building inspection system comprises a set of guide lines 101 and an inspection device 100. The inspection device 100 is configured to move along the guide lines 101 and document the exterior condition of a building.

A rooftop rigging system 901 is configured to suspend the guide lines 101 adjacent an exterior wall of a building. The rooftop rigging system 901 includes a cantilevered section that overhangs the side of the building to position the guide lines 101 appropriately.

A base tensioning system attaches to the other end of the guide lines 101 adjacent the ground. The illustrated base tensioning system incorporates a set of weights 904 and two tensioners 905 that secure the respective guide lines 100 to the weights 904. The weights 904 and tensioners 905 are configured to stabilize the guide lines against wind and other disturbances by maintaining a desirable tension in the guide lines 101. The weights 904 may be coupled directly to the guide lines 101 to form an alternate base tensioning system where the tensioners are omitted and guideline tension may be adjusted at the roofing rigging system.

The building inspection device 100 is configured to move along the guide lines 101 and document the condition of a building exterior. The inspection device 100 comprises a drive train, which propels the inspection device 100 along the guide lines 101, and an imaging system 204 that captures images of the building. An onboard control system is configured to control the drive train and the imaging system 204. The control system regulates movement of the inspection device 100 and documentation of the building condition.

The inspection device drive train comprises a set of wheels 201 and a drive motor 801. The wheels 201 are configured to grip one of the guide lines 101. The drive train wheels 201 include at least one drive wheel that is coupled to the motor 801. The drive train motor 801 is configured to rotate the drive wheel to propel the inspection device along the guide line 101.

The drive train wheels 201 define a path for a guide line. One of the drive train wheels 301 may be biased toward another drive train wheel 201 on an opposing side of the guide line path to create a frictional grip on the guide line 101. The wheel may be biased by a spring (present, but not shown, in the embodiment illustrated in FIGS. 3 and 3a), a tensioner 302 (as illustrated in FIGS. 2 and 2a) or another suitable biasing mechanism.

The drive train illustrated in FIGS. 3 and 3a comprises two drive wheels that are coupled to the same drive motor. The drive wheels are configured to rotate in opposing directions. A path for a guide line is defined between the drive wheels, with one drive wheel being disposed on either side of the path. The two drive wheels having a deformable, high friction outer hoop surface to increase a frictional grip on a guide line disposed in the guide line path.

The drive wheels 201 illustrated in FIGS. 2 and 2a are disposed in a staggered arrangement that creates a tortuous path for the guide line to pass through. The tortuous path of the guide line 101 increases the contact surface area between the guide line 101 and the drive wheel, improving frictional gripping between the drive train and the guide line 101.

The inspection device 100 has a body 102 that supports the imaging system 204, drive train and other components, such as batteries and memory (used to store documentation of the building's exterior condition captured by the imaging system). Three possible configurations of the inspection device body are illustrated in FIGS. 1 to 8 and FIGS. 9 and 10.

The embodiments of the inspection device illustrated in FIGS. 1 to 4 and FIGS. 5 to 8 comprises a main body 102 that supports the inspection device components and an outrigger that extends outwardly transverse to the body 102. The body 102 couples to one guide line 101 and the outrigger couples to another guide line 101.

A set of stabilizing runners 202 is disposed on the outrigger. Another set of stabilizing runners 203 is disposed on the body 102 of the inspection device. The illustrated stabilizing runners 202, 203 comprise wheels with a similar configuration to the drive train wheels 201. The stabilizing runners are not driven in the illustrated embodiment, although it may be desirable to drive more than one set of wheels (such as the stabilizing runners) where more weight is supported on the inspection device.

The illustrated stabilizing runners 202, 203 are configured to grip a guide line 101 to support the inspection device in an upright plane. The drive train wheels 201 and the stabilizing runners 203 disposed on the inspection device body are spaced either side (below and above in the figures) the outrigger wheels 202. Preferably, the drive train wheels 201 and body runners 203 define a path for the weight-bearing guide line that intersects the centre of mass of the inspection device.

Figure 10:
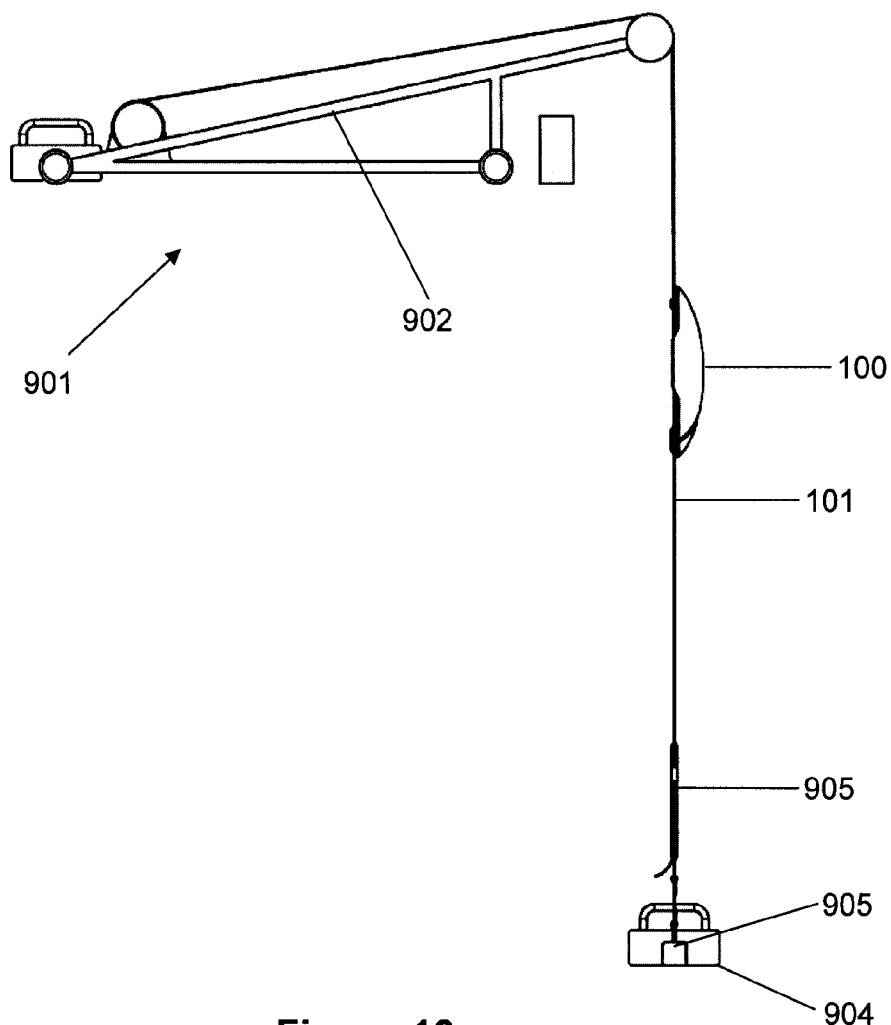
FIG. 10 is a schematic side elevation of the inspection device system illustrate in FIG. 9.
Figure 9:
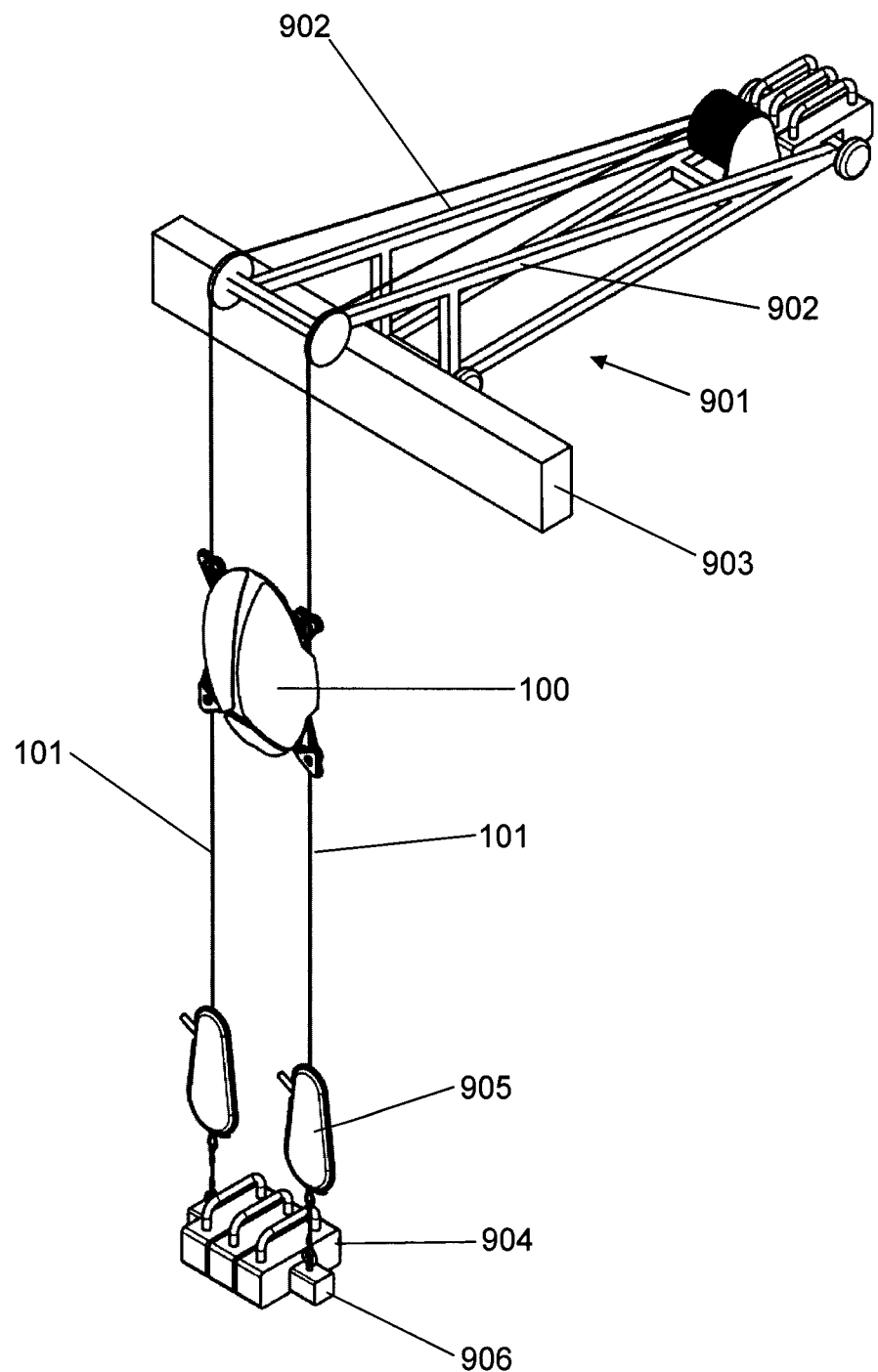
FIG. 9 is a schematic perspective view of an inspection system comprising an inspection device, a pair of guide lines, a rooftop rigging system and a base tensioning system. The inspection device comprising four sets of wheels disposed in an orthogonal arrangement at the extremities of the inspection device body.

Another embodiment of inspection device is illustrated in FIGS. 9 and 10. The inspection device 1100 comprises a body that spans between two spaced guide lines 101. Four sets of are disposed on the body of the device. The sets of wheels are disposed at the extremities of body, so that two sets of wheels grip each guide line 101.

The inspection device control system autonomously controls movement of the inspection device and documentation of a building's exterior condition. For still imagery systems (such as still camera's and sonar based imaging), the control system moves the inspection device between discrete imaging locations, which are defined in part by the capabilities of the imaging system. At each imaging location the control system operates the imaging system to capture and document the condition of the building while retaining the inspection device substantially stationary with respect to the guide lines.

The inspection device preferably includes a communications link which enables the device to couple to a remote terminal. The communications link may relay imagery from the imagining system to the remote terminal or facilitate remote operation of the drive train or imaging system by interfacing the control system with the remote terminal.

An operator generally sets up the rigging system before the inspection system is activated to document a structure. The manual set up includes suspending the guide lines alongside the structure from a suitable support (usually the roof of the structure being documented) and coupling the inspection device to the guide lines. The operator may also move rigging system about the structure to capture images of other areas.

The device is preferably coupled to the lines at a lower end near the ground. Once coupled to the guide lines, the device is calibrated by setting a drive increment that defines the distance between adjacent imaging locations. The operator may calibrate the device or the control system may initiate a self calibration sequence before the imaging process begins.

The drive increment calibration is generally based on the capabilities of the imagining system, the distance of the inspection device from the structure and any other considerations that influence the imaging area captured by the imaging system. The operator may measure the spacing of the inspection device from the structure and input the measurement into the inspection device control system. Generally, the spacing of the inspection device from the wall is used to determine the inspection device drive increment. However, the control system may be capable of determining the drive increment by executing an iterative calibration sequence.

Once the system is physically set up by the operator, the on board control system is activated. The control system may determine the drive increment based on parameters (such as spacing from the structure) input by the operator or initiate an calibration sequence that captures a number of test images at various spacing's along the guide lines to provide an optimal drive increment. The drive increment may be validated at intervals during imaging. A drive increment may not be necessary for continuous imaging systems (such as motion cameras).

One method the inspection device control system may employ to document the structure involves propelling the inspection device along the guide lines between discrete imaging locations, retaining the inspection device in position at each imaging location and capturing an image of the structure. The control system propels the device by activating the drive train motor. The device may be retained at an imaging location by simply deactivating the drive train motor (for motors with braking capabilities) or deactivating the motor in conjunction with applying an auxiliary brake (as illustrated in FIG. 2).

The inspection device control system preferably determines when the imaging sequence is complete for a strip of the structure defined by the guide lines. The end of sequence determination may be based on displacement of the inspection device along the guide lines. The device may execute an initiation sequence prior to each imaging sequence to quantify the length of the strip being imaged. An initiation sequence capable of being executed by the inspection device control system may comprise:

a. propelling the inspection device from a start location toward one end of the guide lines,
 b. recording an indication of travel displacement along the guide lines,
 c. detecting an end of travel condition that defines a travel limit for the inspection device in one direction,
 d. initiating an imaging sequence after the travel limit has been detected, the imaging sequence moving the inspection device away from the travel limit toward the start location,
 e. recording an indication of displacement from the travel limit and calculating an indication of displacement from the start location, and
 f. stopping the inspection device when the control system calculates that the device has returned to the start location.

One embodiment of the inspection device is shown in FIGS. 1-4. The inspection device 100 attaches to guide lines 101 that are suspended alongside a building. The guide lines 101 may be suspended from the building roof or another suitable support by a rigging system. A rooftop rigging system 901 is shown in FIGS. 9 and 10. The arms 902 of the rigging system 901 extend out beyond the edge of the building 903 so that the vertical portions of the guide lines 101 are positioned at a distance from the side of the building. For example, they may be 2-3 meters from the building. Tension weights 904 may be attached to the lower ends of the guide lines 101 located near the ground, as illustrated in FIGS. 9 and 10, to maintain tension in the guide lines 101.

The inspection device 100 has a body 102 made of a suitable material, such as plastic. A line attachment system projects from the underside of the body 102. In the embodiment shown in FIG. 2, the line attachment system comprises three sets of wheels. These sets of wheel are: the drive train wheels 201, positioned near the top of the inspection device body 102; the lower stabilizing runners 203 positioned near the bottom of the inspection device body 102; and the outrigger stabilizing runners 202 located toward a lateral edge of the inspection device 101 and disposed longitudinally between the drive from wheels 2001 lower runners 203. The drive train wheels 201 and the lower stabilizing runners 203 attach to one guide line 101, which is the weight-bearing guide line. The outrigger wheels 202 attach to a stabilizing guide line 101 which is suspended alongside the weight bearing guideline. The outrigger wheels 202 and the stabilizing guide line orientate the inspection device imaging system relative to the structure. Other stabilizers may be used orientate the inspection device.

Preferably, the drive train wheels 201 and lower stabilizing runners define an axis that intersects the centre of mass of the inspection device 100 or a point near the centre of mass, so that the weight bearing guide line is disposed close to the inspection device centre of mass to minimize rotational imbalances. The outrigger stabilizing runners 202 attach to another guide line 101 and align the underside of the inspection devices body with the side of the building.

The drive train wheels 201 are shown in isolation in FIG. 2a. In this embodiment, three wheels are used. One of the illustrated wheels is a drive wheel that is coupled to a drive motor. A tensioner 302 biases one of the drive train wheels 301 inwardly toward the other wheels 201 to ensure that the drive wheel is in high frictional contact with the guide line 101. A spring or other suitable biasing mechanism may be substituted for the illustrated tensioner. Tension can be applied to the wheel 301 either mechanically by the operator or through an electronically actuated clutch. The use of a tensioner facilitates installing and removing the vehicle from the line path. When engaged, the mechanical system creates adequate friction between the drive train wheels and the line. This arrangement wherein the drive train wheels are releasably attached to the guide lines 101 avoids the need to thread the guide lines 101 through winders, and the inspection device 100 can easily be attached or removed from the guide lines 101 at any point along the guide lines 101.

The inspection device drive train incorporates a drive motor 801, drive train wheels 201 (including at least one drive wheel), and a geared transmission between the drive motor and drive wheel. The drive train may include more than one motor and any suitable transmission. The motor 801 drives the drive wheel to move the inspection device 100 up (raising the inspection device 100) or down (lowering the inspection device 100) along the guide lines 101. FIG. 4 show the top of the inspection device 100 with its outer cowling removed to show the arrangement of components disposed on the body 102.

In the depicted embodiment, the lower stabilizing runners 203 and the outrigger runners use one guide wheel on either side of the guide line 101. A wheel tensioner clamps the runners around the respective guide lines 101.

An imaging device is positioned within the body 102 so that it may transmit and/or receive imaging signals through the underside of the body 102 to inspect a portion of the side of the building. In the embodiments shown in FIGS. 1-8, the imaging device is a still camera 204, 803. An opening on the underside of body 102 accommodates the camera lens. A photosensitive device, such as a CCD or CMOS image sensor, captures an image from light reflected from a portion of the wall of the building that is focused by the lens. The field of view depends on the lens and the distance of the inspection device 100 from the wall. For example, the inspection device 100 and lens may be located 2.4 meters from the wall, in which case the camera may capture an image representing a portion of the wall approximately two meters square, depending on the focal length of the lens and size and aspect ratio of the sensors.

Another inspection device is illustrated FIGS. 5 to 8. The inspection device 1000 has an alternate drive train and component arrangement. The batteries 804 are illustrated on the underside of the device, partially offsetting the weight of components disposed on the upper side of the inspection device body and distributing mass about the guide lines 101.

The inspection device 1000 drive train comprises four drive train wheels 201. Two of the drive train wheels 201 (the drive wheels 301) are driven by the drive motor 801. The drive wheels are coated with a high friction (such as rubber) to improve the drive train grip on the weight bearing guide line. The wheel coating may also be resiliently deformable to increase the contact surface area between the drive wheels 301 and the guide line 101.

One of the drive wheels is coupled to the motor by a bevel gear. This is the primary drive wheel. The rotational axis of the primary drive wheel is locked adjacent the drive motor. The other drive wheel (the secondary drive wheel) is coupled to the primary drive wheel by a chain or belt. The secondary drive wheel is supported within a slider. The slider allows the axis of rotation of the secondary drive wheel to translate perpendicular to the guide line path so that the drive wheels may be separated for insertion of the weight bearing guide line 101. The secondary drive wheel is biased toward the primary drive wheel by a spring, creating a frictional grip on a guide line disposed in the guide line path. The spring acts between a slider bracket that supports the secondary wheel and a slider housing that is held relative to the inspection device body.

The chain or belt that rotates the secondary drive wheel is arranged in a loop that incorporates a tensioner. The tensioner accommodates movement of the secondary drive wheel without compromising operation of the drive train. The looped chain bisects the two drive wheels and drives the secondary drive wheel in an opposing rotational direction (clockwise/ anticlockwise) to the primary drive wheel so that the drive wheels cooperate to move the inspection device along the weight bearing guide line.

The other two drive train wheels are runners. The drive train runners reduce the tendency for the weight bearing guide line 101 to tangle around one of the drive wheels 301. The drive wheels 201 and lower stabilizing runners 202 define a path for the weight bearing guide line 101 that bisects the batteries 802. Preferably the guide line path intersects the centre of mass of the inspection device.

In order to determine the position of the inspection device 100 on the line, quadrature encoders may be used to get a relative position. These are highly accurate and can give excellent positional feedback. The system will be able to give a relative displacement from a known fixed "zero" position. This should be accurate within less than 1 inch.

Alternatively, or additionally, other means may be employed to determine the position of the inspection device, such as placing spaced marks on the guide line and using an optical sensor to detect the marks, or using GPS.

The motor 801 may be, for example, a 12, 24, or 48 VDC brushless motor, which may be a stepper motor. Preferably, the motor incorporates a brake that stops the drive train from slipping when the motor is not being driven by the control system. Passive motor braking may allow the inspection device to retain a desired position on the guide lines without an auxiliary braking system. One type of passive braking motor is an AC sliding rotor motor. The precise requirements for current rating and torque ratings can be determined for particular applications and component weights.

Figure 11:
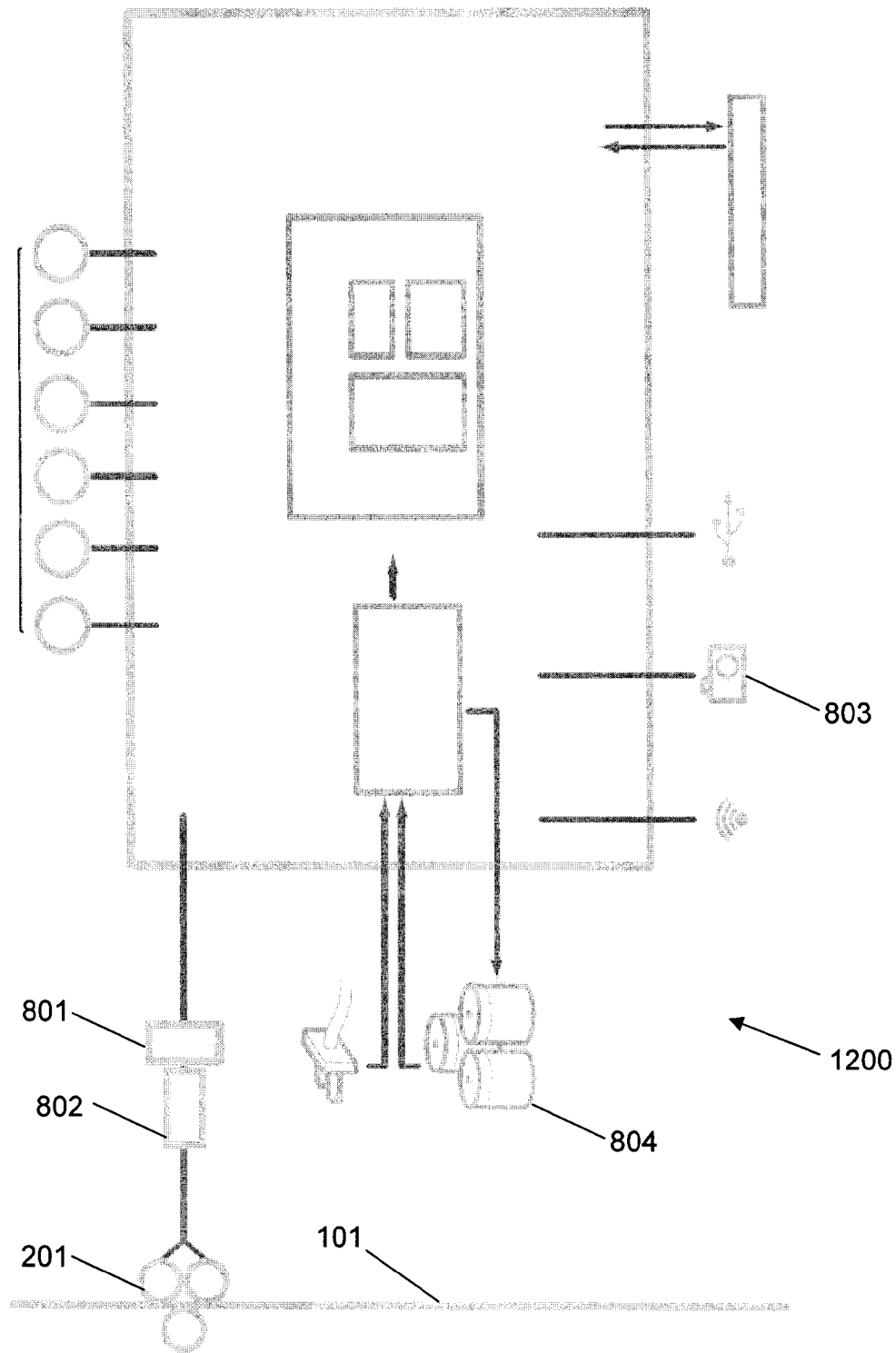
FIG. 11 is a schematic diagram of a control system for an inspection device.

The inspection device control system 1200 is shown schematically in FIG. 11. The controller may comprise a single-board computer running an embedded operating system, preferably with a fast boot time and fast on-board data storage, such as flash memory.

The control system 1200 may have one or more processor, with a memory bank 1213. The processor may be a general purpose processor, or CPU, programmed by software or may be a purpose-built hardware processor for implementing the specific functions that the inspection device 100 performs. The control system 1200 is responsible for controlling the imaging system (camera 803 in the illustrated embodiment) and the movement of the inspection device 100 along the guide lines 101 by directing the motor 801 to drive the drive wheel 203 via the gearbox 802. The system controller may contain peripheral connections required for integration with a servo amplifier, quadrature encoder, over-limit sensor (current, position), and on-board user-interface components.

The system controller may also control an auxiliary brake 205 (as shown in FIG. 2) that may straddle the weight-bearing guide line 101 to which the drive wheel is adjacent. When activated, the brake may clamp the guide line 101, thereby preventing any movement of the inspection device until the brake 205 is released. The inspection device 100 may be operated autonomously once it is attached to guide lines 101. For safety reasons, the brake may be designed to be closed and clamped to the line when the inspection device is not being driven and opened when the drive train is activated.

The processor, motor 801 and imaging system 803 may be powered by batteries 804 carried by the inspection device. Alternately, the device may receive power through a guide line or other line extending from the inspection device 100 to the rooftop or ground or other location where a suitable low-voltage power can be located.

The inspection device 100 may employ collision avoidance systems to avoid damage as it reaches the end of the guide lines 101 or if obstacles obstruct the vehicle path during automated or semi-automated (blind) operation. Collision avoidance may be achieved with short-range ultrasonic sensors or physical bumpers that detect obstacle contact.

The inspection device 100 may also employ "end of travel" sensors for sensing when the vehicle has reached the end of the guide lines. This may employ mechanical contact sensors that interact with an intentional obstruction to the line path—for example a machined cylindrical "stop" that is installed on site at adjustable positions along the line. The device may alternatively be able to sense when the line shape changes or provide a mechanical stop that bumps against the rigging and provides an interrupt signal to the motor power on the vehicle.

The inspection device may incorporate a guide line tension detector, a battery charge detector, an over temperature detector, an over-current detector or other systems to support operation of the device and provide information to the control system.

The inspection device is deployed by being attached to a rooftop rigging system 901, 1001 so that the underside of the body 102 faces the wall of the building and the imaging system is suitably positioned to capture a portion of the wall of the building adjacent to the inspection device. For example, if the imaging system is a motion camera, the inspection device can be moved continuously up or down the length of the wall being analyzed and capture video images of the strip. The width of the strip is determined by the field of view of the video camera.

If the inspection device employs a still camera that, for example, has a field of view two meters square at the surface of the building, then the inspection device control system may raise or lower the inspection device in increments of somewhat less than two meters (e.g. 1.8 meters) and the inspection device may take a photograph at each imaging location so that the centers of successive photographs are separated by 1.8 meters, thereby imaging a strip of the wall two meters wide. The inspection device may document a strip of wall be moving between discrete imaging locations where the camera captures image of the wall. The rooftop rigging system may then be shifted laterally, by 1.8 meters for example, after each successive vertical strip has been documented.

Each photograph may be tagged with the time and location at which it was taken. The location may be ascertained from quadrature encoders, or other suitable means. The series of photographs (or video in the case the imaging device is a video camera) is preferably stored in on-board memory associated with the system controller for retrieval and analysis after the scanning has been completed.

Adjacent images may be stitched together by correlating the overlapping regions and suitably warping the images (e.g. to account for wind deflection of the inspection device), so that problem areas falling in more than one image may be examined more easily. The images may be stitched together by software on an external computer that the images are transferred to after imaging is completed.

In one mode of operation, the inspection device may be programmed so that it may be attached to the guide lines 101 near the ground, and then autonomously inspect an entire strip of the building from the point it is attached to the top of the building with a width equal to the width of the field of view (at the wall) of the imaging device. It may first climb directly to the top of the building, where it stops. The system controller may then instruct the camera to take a photograph, store that photograph in a memory, and then operate the drive train to cause the inspection device to move downward by, for example, 90% of the height of the field of view of the imaging system. This process may then be automatically repeated until the inspection device returns to the ground with of the strip of the wall documented and stored in on-board memory.

The inspection device 100 may include a wireless connection to provide connectivity back to a ground-based (or rooftop based) computer, for example, via wireless Ethernet, using standard components chosen for their low-power consumption and ability to work in an ad-hoc mode (i.e. communicate directly with one another without need for a wireless router)

The weight of the vehicle, including batteries, is supported by the body of the inspection device transmitted to the guide lines (predominantly the weight-bearing guide line). It is desirable to reduce the vehicle weight in order to improve scanning duration. High-capacity lithium ion batteries may be preferred for improved power to weight characteristics.

The system controller may provide a user interface to allow an operator to control the vehicle, either in an automated or manual fashion, for example through controls located on the inspection device, or by a wireless connection to a laptop computer.

In another embodiment shown in FIG. 12, the inspection device drive train incorporates a belt drive. In the illustrated embodiment, the belt drive comprises two belts disposed on either side of the guide line path. Each belt extends around a drive wheel and an associated runner. The coupled wheels are arranged generally parallel with the guide line path so that the weight-bearing guide line is gripped between the respective belts. One pair of coupled wheels is biased toward the guide line path by a wheel tensioner 302.

In some embodiments, such as those devices 900, 1002, 1100 shown in FIGS. 9 and 10, the inspection device may incorporate four sets of wheels, two sets of wheels griping each guide line to distribute the weight of the inspection device evenly between lines. The drive train may incorporate a single drive wheel on one side of the device or a drive wheel on either side. Preferably, where multiple drive wheels are utilized, the drive wheels are coupled and driven synchronously to propel the inspection device up or down the guide lines without significant rotation.

Line tensioning devices 905, as shown in FIGS. 9 and 10, may be employed to attach the line tension weights 904 to the ends of the guide lines 101. A spreader 906 may be used to maintain a suitable separation between the guide lines 101 that correspond to the arrangement of the inspection device wheels.

The size and weight of the inspection devices may vary depending on the imaging system employed and various other factors. The embodiment as depicted in FIGS. 1 to 8 is approximately 860 mm high and 837 mm wide, and weighs about 10 kg. With suitable motors and gearing the inspection device 100 may be able to travel and inspect a strip 20 floors high in about one minute for example, expending approximately 100 watts per minute of power.

It will be appreciated that imaging systems other than optical cameras may be employed. For example, x-ray, sonar, infrared, radar, electromagnetic flux generators, or magnetic eddy sensors, or a combination of such systems may be used to document the exterior condition of the building. For example, the imaging system may incorporate two cameras to cover a wider area, or cover the same area from different angles to allow the construction of three dimensional views of the surface of the wall that can be used to identify protrusions and other depth variations. A focused ultrasonic scanning system or similar device could also be use in conjunction with a camera to produce a three-dimensional map of the surface of the wall.

The system controller may be programmed to analyze the captured data and may transmit the collected data to a terminal where a person or software may analyze it. For example, the controller may analyze collected images and automatically identify irregularities and then transmit such findings to a computer on the ground or in the building.

Although the invention has been primarily described using example embodiments that employ two vertical guide lines, the invention is no so limited. The invention requires only a single, weight-bearing, guide line, which may be vertically oriented using tension weights, as described in the above embodiments and FIGS. 1-8, or it may be otherwise oriented and anchored. For example the weight-bearing guide line may be anchored to the ground so that the guide line is at a certain angle relative to the vertical, which may be useful for buildings with sloped sides. Alternatively the weight-bearing guide line could be oriented horizontally or on an angle, so that the inspection device may move from side to side across the building. In addition to at least one weight-bearing guide line, an aligning system that orientates the inspection device relative to the building (so that the underside of the inspection device faces the side of the building) is also required. One such alignment mechanism, in embodiments with a central vertical weight-bearing guide line, is a second vertical guide line towards a lateral edge of the inspection device, as shown in the embodiments in FIGS. 1-8. Another alignment mechanism is shown in FIGS. 9 and 10, which consists of a second weight-bearing guide line, where the two guide lines are positioned towards the lateral edges of the inspection device. Other alignment mechanisms may alternately be employed. For example, a single flattened weight-bearing guide line may be employed with modified guide wheel assemblies designed to prevent rotational motion of the inspection device, or an outrigger system that contacts the building (preferably with rollers) to prevent mis-orientation of the device.

The foregoing description illustrates only certain preferred embodiments of the invention. The invention is not limited to the foregoing examples. That is, persons skilled in the art will appreciate and understand that modifications and variations are, or will be, possible to utilize and carry out the teachings of the invention described herein. Accordingly, all suitable modifications, variations and equivalents may be resorted to, and such modifications, variations and equivalents are intended to fall within the scope of the invention as described and within the scope of the claims.

The invention claimed is:

1. An inspection device for inspecting an exterior side of a structure, a first weight-bearing guide line and a second guide line being suspended vertically alongside the side of the structure and spaced away from the side of the structure, the inspection device comprising:
   a body;
   an imaging system attached to the body and configured to image a portion of the side of the structure proximate to the inspection device;
   a drive train attached to the body, the drive train comprising a first set of wheels, including a drive wheel, the wheels being configured to grip the first weight bearing guide line, and a drive motor coupled to the drive wheel to rotate the drive wheel and propel the inspection device up and down the first weight bearing guide line;
   a stabilizer configured so that the inspection device and imaging system are maintained in a substantially fixed orientation and spaced away from the side of the structure; and
   a control system attached to the body and coupled to the drive train, the control system being configured to autonomously control the movement of the inspection device up and down the guide lines.

2. The inspection device of claim 1, wherein the stabilizer comprises a second set of wheels or runners attached to the body and spaced horizontally from the first set of wheels, the second set of wheels being configured to grip the second guide line and move up and down the second guide line as the drive wheel propels the inspection device up and down the first weight bearing guide line.

3. The inspection device of claim 2, wherein the second guide line is also weight-bearing and wherein the first set of wheels and the second set of wheels are horizontally spaced apart and positioned to distribute the weight of the inspection device approximately evenly between the two guide lines.

4. The inspection device of claim 3, wherein the drive train comprises another drive wheel, which is part of the second set of wheels, and the drive wheels are coupled and driven synchronously to propel the inspection device up and down the guide lines without significant rotation of the device.

5. The inspection device of claim 2, further comprising a set of central runners that are vertically displaced from and aligned with the first set of wheels, the central runners being configured to grip the first weight bearing guide line, the first set of wheels and the central runners defining an axis that intersects the centre of mass of the inspection device or a point near the centre of mass, so that the first weight bearing guide line is disposed close to the centre of mass of the inspection device, and wherein the second set of wheels or runners are runners that act as guide wheels.

6. The inspection device of claim 5, further comprising an outrigger attached to the body that extends away from the centre of mass of the inspection device, wherein the second set of wheels or runners are attached to the outrigger at a position spaced horizontally away from the centre of mass of the inspection device.

7. The inspection device of claim 1, wherein the side of the structure is vertical so that the inspection device and imaging system are maintained at a substantially fixed distance from the side of the structure as the device moves up and down the guide lines.

8. The inspection device of claim 7, wherein the inspection device and imaging system are maintained at a substantially fixed distance from the side of the structure that is greater than one meter.

9. The inspection device of claim 7, wherein the inspection device and imaging system are maintained at a substantially fixed distance from the side of the structure that is greater than two meters.

10. The inspection device of claim 1, wherein the drive train wheels define a path for the weight-bearing guide line, one drive train wheel being biased toward another drive train wheel on an opposing side of the weight-bearing guide line path to create a frictional grip on the weight-bearing guide line when disposed in the path.

11. The inspection system of claim 1, wherein the drive train comprises two drive wheels that are coupled to the same drive motor and configured to rotate in opposing directions, the drive wheels defining a path for the first weight-bearing guide line and being disposed on opposing sides of the first weight-bearing guide line path, the drive wheels having a deformable, high friction outer hoop surface to increase a frictional grip on the first weight-bearing guide line disposed in the first weight-bearing guide line path.

12. The inspection device of claim 1, further comprising a battery supported by the body that supplies power to the inspection device, and a memory supported by the body for storing documentation of the structure's exterior condition captured by the imaging system.

13. The inspection device of claim 1, wherein the control system is configured to autonomously:
move the inspection device between discrete imaging locations by operating the drive train, the imaging locations being defined in part by the capabilities of the imaging system;
retain the inspection device in a substantially stationary position with respect to the guide lines at each imaging location; and
operate the imaging system to document the condition of the side of the structure at each imaging location.

14. The inspection device of claim 1, wherein the imaging system is a still camera.

15. The inspection device of claim 1, wherein the imaging system is a motion camera.

16. The inspection device of claim 1, wherein the imaging system is a sonar imaging system.

17. A method of documenting the condition of a side of a structure, the method comprising:
coupling the inspection device of claim 1 to a first weight-bearing guide line and a second guide line suspended vertically alongside the side of the structure and spaced away from the side of the structure;
calibrating the inspection device by setting a drive increment, the drive increment defining the distance between adjacent imaging locations;
propelling the inspection device along the guide lines between discrete imaging locations;
retaining the inspection device in position at each imaging location and capturing an image of the structure using the imaging system; and
determining imaging sequence completion for a strip of the structure defined by the guide lines.

18. The method of claim 17, further comprising moving the rigging system about the structure and capturing images of adjacent strips.

19. An inspection system for inspecting an exterior side of a structure, the inspection system comprising:
(a) a guide line being designated to be a first weight-bearing guide line;
(b) a second guide line;
(c) a rooftop rigging system configured to suspend the guide lines vertically alongside the side of the structure and spaced away from the side of the structure, the rigging system comprising a cantilevered section that is configured to overhang the side of the structure to position the guide lines;
(d) a base tensioning system configured to couple to an end of each of the guide lines spaced from the rooftop rigging system, and to stabilize the guide lines alongside the structure; and
(e) an inspection device comprising:
a body;
an imaging system attached to the body and configured to image a portion of the side of the structure proximate to the inspection device;
a drive train attached to the body, the drive train comprising a first set of wheels, including a drive wheel, the wheels being configured to grip the first weight bearing guide line, and a drive motor coupled to the drive wheel to rotate the drive wheel and propel the inspection device up and down the guide lines;
a stabilizer coupled to the second guide line and configured so that the inspection device and imaging system are maintained in a substantially fixed orientation and spaced away from the side of the structure; and
a control system attached to the body and coupled to the drive train, the control system being configured to autonomously control the movement of the inspection device up and down the guide lines.

20. The inspection system of claim 19, wherein the inspection device stabilizer comprises a second set of wheels or runners attached to the body and spaced horizontally from the first set of wheels, the second set of wheels being configured to grip the second guide line and move up and down the second guide line as the drive wheel propels the inspection device up and down the guide lines.

* * * * *